United States Patent [19]

Shaffer et al.

[11] 3,932,516
[45] Jan. 13, 1976

[54] NOVEL OXYGENATED DERIVATIVES OF THUJOPSENE

[75] Inventors: Gary W. Shaffer; Garry C. Kitchens, both of Wayne; Kent Kaiser, Pequannock, all of N.J.

[73] Assignee: Givaudan Corporation, Clifton, N.J.

[22] Filed: Oct. 19, 1973

[21] Appl. No.: 408,127

Related U.S. Application Data

[62] Division of Ser. No. 49,950, June 25, 1970.

[52] U.S. Cl. ......... 260/586 F; 204/158 R; 252/522; 260/348 C; 260/488 B; 260/586 P; 260/617 F; 260/617 H; 260/631.5; 260/666 PY; 260/675.5
[51] Int. Cl.$^2$ ......................................... C07C 49/36
[58] Field of Search ............. 260/586 R, 587, 586 F

[56] References Cited
UNITED STATES PATENTS

| | | | |
|---|---|---|---|
| 1,946,115 | 2/1934 | Schoeller et al. | 260/587 X |
| 3,072,709 | 1/1963 | Saucy | 260/586 R X |
| 3,560,571 | 2/1971 | Kropp | 260/586 R |

OTHER PUBLICATIONS

Chem Abstracts, Vol. 69, p. 66973a, (1968)

*Primary Examiner*—Norman Morgenstern
*Attorney, Agent, or Firm*—Thomas Cifelli, Jr.

[57] ABSTRACT

There are provided novel oxygenated pentamethyldecalins and dehydro derivatives thereof which are lasting odorants of woody character and which are useful in the perfumery art.

These novel compounds are prepared by oxidation of cis-thujopsene and cis-dihydrothujopsene which are readily available products of natural origin.

1 Claim, No Drawings

NOVEL OXYGENATED DERIVATIVES OF THUJOPSENE

This is a division of application Ser. No. 49,950 filed June 25, 1970.

DESCRIPTION OF THE PRIOR ART

Cis-thujopsene, the starting material in the present invention is a readily available natural product. It may be reduced to cis-dihydrothujopsene by methods well known in the art. (Erdtman and Norin, *Acta. Chem. Scand.*, 13, 1124 (1959); Forsen and Norin, ibid, 15, 592 (1961); Norin, ibid, 15, 1676 (1961); Erdtman and Norin, Chem. and Ind., 622 (1960)).

Thujopsan-2-one, similarly a starting material herein is prepared by oxidation of cis-thujopsene according to the method of Ohloff and Strickler (German application Ser. No. 1,911,440), and of S. P. Acharya and H. C. Brown (5th International Symposium of the Chemistry of Natural Products, London, July 8–19, 1968, p. 294).

SUMMARY OF THE INVENTION

The present invention concerns the conversion of the readily available natural product cis-thujopsene (V) and its close derivative cis-dihydrothujopsene (VI) into three novel ketones and one epoxide of related structure and similar olfactory activity.

Cis-dihydrothujopsene (VI) is converted into cis-4a, 5,6,7,8,8a hexahydro-3,4a, 5,5,8a-pentamethyl-2 (1H)-napthalenone (I) referred to herein below as the pentamethyloctalone (I) by two different routes. The same compound may also be prepared starting with cis-thujopsene (V) and also from cis-thujopsan-2-one (XV) by a method related to this latter route.

In the first method, cis-dihydrothujopsene (VI) is oxidized to the pentamethyloctalone (I).

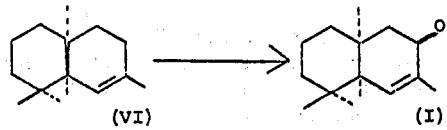

The reactants are taken up in an anhydrous reaction inert polar solvent and treated with an excess of oxidant, suitably of the chromate species at moderate temperatures.

The following flow chart illustrates the method starting with cis-thujopsene (V)

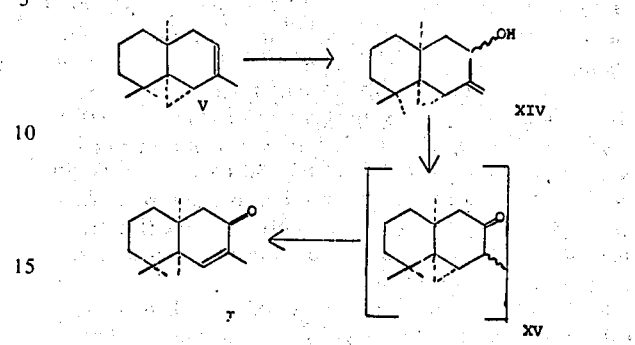

In this modification cis-thujopsene (V) is taken up in a suitable solvent and irradiated in the presence of oxygen and a carrier dye. The color of the dye should be the complement of at least a portion of the wavelength range of the irradiation source, that is to say the dye should absorb light in that wave length range.

After irradiation the product is reduced with a chemical (i.e., not catalytic) reducing agent to yield intermediate enol (XIV). Enol (XIV) is then contacted with a surface active catalyst such as alumina, or the like which is believed to cause the enol (XIV) to give the ketoform (XV) which is then rearranged to yield the pentamethyloctalone (I). This rearrangement is conveniently achieved by eluting the enol (XIV) from a column packed with the catalyst. The eluant should be sufficiently polar to achieve elution within a reasonable number of column volumes but not so polar as to cause elution which is too rapid to permit proper contact with the catalytic material.

It will be seen that the unisolated keto intermediate (XV) is in fact cis-thujopsan-2-one, which is a readily available product. Hence starting with the thujopsan-2-one, compound (I) may be produced by similar contact with a surface active catalyst.

The following flow chart (I) shows how cis-dihydrothujopsene may be converted into pentamethyl octalone (I).

CHART I

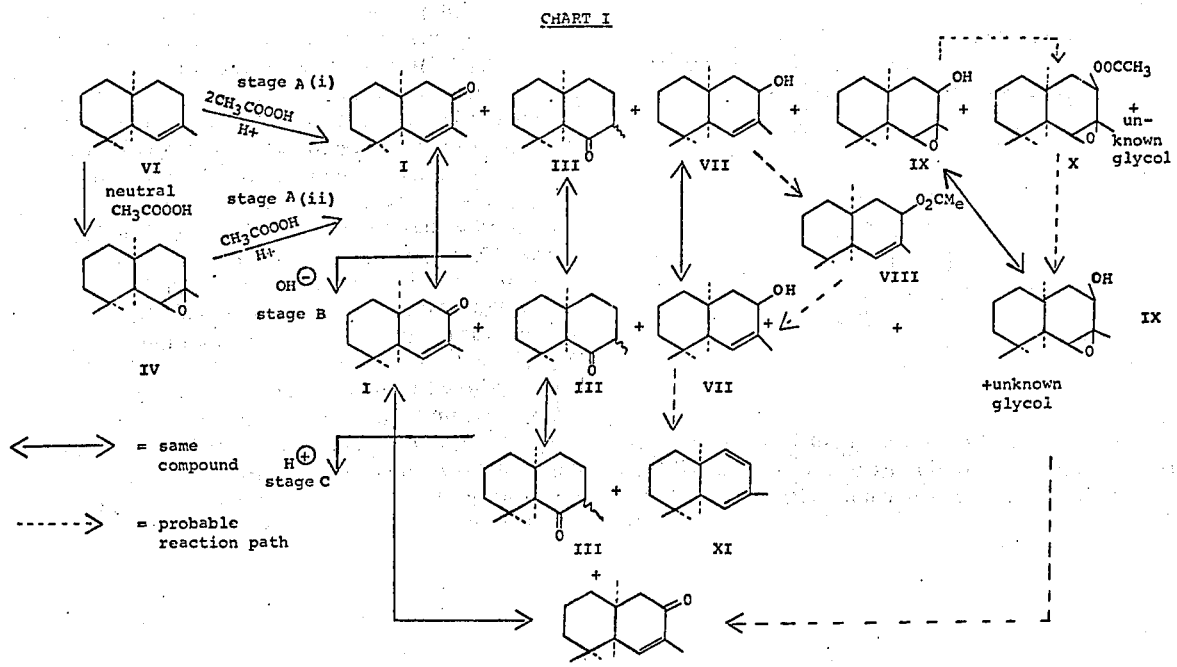

In stage A (i) cis-dihydrothujopsene (VI) is treated with a peracid in the presence of hydrogen ion to yield a mixture of compounds indicated by formulas (I), (III) and (VII) thru (X). The reaction product is spearated from the reaction mixture, suitably by extraction with a water immiscible solvent. Separation of the components at this stage is not required.

The entire mixture is then treated with a strong base in an alkanol in stage B. In this step products (I), (III), (VII) and (IX) are unchanged, however, it is presumed that (VIII) is converted to (VII) and (X) is converted to (IX). The entire reaction product is again separated from the reaction mixture, suitably by solvent extraction, however, here again resolution of the respective components is not necessary.

In stage C the reaction product of stage B is treated with a strong acid in an anhydrous solvent, suitably under continuous distillation to remove the water/solvent azeotrope.

Compound (I) and Compound (III) are unchanged, while the 3-hydroxypentamethyloctahydronapthalene (VII) is converted into the pentamethylhexahydronapthalene (XI), and the 3-hydroxy-1,2-epoxy-pentamethyldecalin (IX) is converted into compound I.

The ratio of the products I: III: XI is of the order of 25:10:1. This result is most surprising since (I) and (XI) would not normally be expected to be formed in this reaction series. The three identified compounds I, (III) and (XI) constitute ca. 80% of the recovered product.

In an alternative procedure cis-dihydrothujopsene (VI) is reacted with neutral peracid, that is to say peracid having substantially no hydrogen ions present, to form cis-decahydro-1,2-epoxy-2,4a,8,8,8a-pentamethylnapthalene (IV), hereinafter referred to as the epoxypentamethyldecalin (IV). This may then be converted in stage A (ii) to the same products as above by the same means.

As mentioned in connection with step A (ii) above, cis-dihydrothujopsene (VI) is readily converted into the corresponding 1,2-epoxide (IV) by a peracid in neutral conditions.

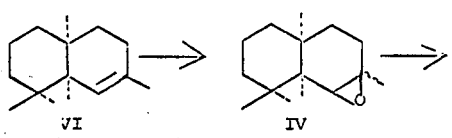

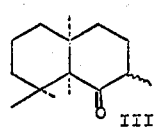

The epoxide (IV) upon treatment with an acid, suitably in anhydrous conditions in an inert atmosphere yields the pentamethyl-1-decalone (III).

The pentamethyl-2-octalone (I) may be hydrogenated to give the corresponding pentamethyl-2-decalone i.e.: cis-3,4,4a,5,6,7,8,8a-octahydro-3,4a,5,5,8a-pentamethyl-2-(1H)-napthalenone (II).

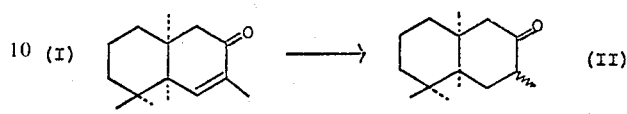

It has been found that compounds I, II, III and IV have valuable properties as odorants in perfume manufacture. The compounds have various woody odours which add body and strength to the odorant compositions to which they are added. They possess valuable fixative properties and possess very useful tenacity.

DESCRIPTION OF THE PREFERRED EMBODIMENTS

Cis-dihydrothujopsene (VI) is oxidized to pentamethyloctalone (I).

In the preferred modification cis-dihydrothujopsene (VI) is taken up in a suitable polar reaction inert anhydrous solvent. It is preferred to use an aliphatic acid and anhydride such as an alkanoic acid and anhydride. The especially preferred alkanoic moities contain 1–5 carbon atoms such as the formic, acetic, propionic, butyric and valeric moieties, however in view of the malodorous properties of certain of the moieties, acetic and propionic acids and anhydrides are the solvents of choice.

There is utilized as an oxidant any available oxidant of the chromate species, especially preferred are the alkali metal dichormates and the alkylchromates such as sodium or potassium dichromate or, for example t-butylchromate.

There is utilized at least the calculated amount of oxidant (i.e. 4 equivalents of oxidant per mole of (VI) however it is preferred to use an excess of oxidant, a two fold excess (i.e. 12 equivalents per mole of (VI) is especially preferred. The concentration of (VI) lies between 0.25 and 0.5 moles/liter of solvent.

The reaction is exothermic. It is therefore preferable to add the oxidant slowly while maintaining the vessel temperature at or below 25°C. After thorough mixing of the reagents the temperature is carefully raised. The temperature may rise to 50°C, however it is preferred to hold the temperature between 30° to 40°C in which range the reaction is self sustaining and will decline upon completion of the reaction. While reaction times will of course vary, generally the addition step should take about 1.5 hours, the stirring step at 25° about 0.5 hours and the reaction step at 40° about 2–5 hours.

The reaction is then quenched and the product isolated. Suitably the reaction mixture is poured into an approximately equivalent volume of water and extracted with a suitable water immiscible solvent and the solvent removed by evaporation.

In the irradiation process using cis-thujopsene (V) as starting material, the thujopsene (V) is taken up in any commonly utilized irradiation solvent. Among these solvents may be included hydrocarbons, ethers, alcohols and the like. However alkanols such as methanol being especially preferred.

The irradiation solution is sparged with oxygen, preferably through a sintered glass plate. The source of oxygen may be pure oxygen or air. The rate of flow is not critical, flow rates of beween 1 and 30 liters per minute have been found satisfactory.

The irradiating source may comprise principally visible light (450–700 nm) or U.V. light (200–450 nm).

With visible light there are used carrier dyes whose colour is a complement of at least a portion of the irradiated wave length range of the irradiation source. As long as these criteria are met, the actual carrier dye used is not critical, however rose bengal, eosin chlorophyll, methylene blue and the like have been found useful.

Where U.V. light is used sensitizers such as benzene, aryl and alkyl ketones or other aromatics may be employed, however the use of high energy sources such as U.V. light is not favored.

The irradiation is carried out between 0° and 50°C, suitably at between 20°–25°C. Irradiation is continued until oxygen uptake ceases. This is determined by a steady, non-increasing value in a hydroperoxide determination.

The irradiated mixture is then reduced, any reducing agent may be used, aqueous sodium sulfite, lithium aluminum hydride and sodium borohydride are especially suitable. It should be noted however that where the solvent used is hydroxylic solvent, lithium aluminum hydride is not suitable. After addition of the reducing agent, more water is added and the product, presumably the enol (XIV) among others is extracted with a suitable water immiscible solvent. The residue obtained is chromatographed on a suitable catalyst.

The catalyst should preferably be neutral alumina, acidic or basic alumina are operative but the yields are not optimal. The catalyst of choice is neutral grade I alumina.

The polarity of the solvent used is important but not totally critical. It should be more polar than hexane and less polar than methanol. Hexane/benzene gives by-products while benzene/ether preferably at a 4:1 ratio gives the desired pentamethyloctalone (I).

While the column ratio is not critical good results have been obtained at a load/column ratio of 1:50 to 1:100.

In accordance with the foregoing catalytic chromatographic procedure, but starting with thujopsan-2-one (XV), the same product is obtained. It should be noticed however that solvents of slightly higher polarity are required to elute the pentamethyloctalone (I).

In the fourth modification of the procedures for the preparation of pentamethyloctalone (I), cis-dihydrothujopsene (VI) is treated with peracid in the presence of hydrogen ion. There may be utilized any peracid, suitably an organic peracid such as peracetic, perphthalic, perbenzoic or metachloro perbenzoic acid. Commercial peracetic acid contains 1% of concentrated sulfuric acid, if other peracids are used, a similar quantity of acid must be added. The quantity is not critical, from 0.2–5% of acid may be added.

While it is preferred to carry out the reaction without solvents, there may be utilized reaction, inert solvents such as benzene, ether, glacial acetic acid or the like.

The reagent medium of choice is 40% aqueous peracetic acid.

There is utilized an excess of peracid, while there is no upper limit to the amount of acid used, it is preferred to use at least 2–3 moles of peracid per mole of dihydrothujopsene (VI).

The acid is warmed with agitation at a temperature of between 10° and 80°C, preferably at between 30° and 40°C for 10–60 mins. preferably for about 20 minutes while the dihydrothujopsene (VI) is added slowly. After addition is complete, agitation at this temperature is continued for about 3 hours, although longer times may sometimes be required to remove the starting material. The reaction mixture is then quenched with water and extracted, suitably with hexane.

The residue from the extraction step is taken up in an alkanol, suitably in methanol and treated with a base, suitably an alkali, such as sodium or potassium hydroxide.

There is utilized from 1–5, suitably about 2 parts by weight of solvent relative to each part of peracid product.

There are utilized 1–5 moles of base per mole of residue, preferably between 1.5–2 moles/mole are used.

While it is not essential to heat the reaction mixture, temperatures between 25° and 100°C or even higher are operative. It is especially convenient to carry out the reaction at the reflux temperature of the solvent. The reaction is run until all of the ester has been saponified, as determined by infrared analysis, 3 hours is usually sufficient for this to occur.

The reaction product is then isolated. In the preferred mode of isolation, water is added to the reaction mixture and methanol removed by distillation until a pottemperature of about 95°C is reached. The mixture is then cooled and extracted with a water-immiscible solvent, hexane being especially suitable. The hexane extract is worked up in the usual manner to leave a saponified residue.

The saponified residue is taken up in a hydrocarbon solvent, preferably a solvent which forms an azeotrope with water such as benzene, toluene or the like. There is added thereto a strong acid, mineral acids or organic acids may be employed, for example sulfuric acid or p-toluene sulfonic acid may be used.

There is employed at least 1 part by weight of solvent per part by weight of saponified residue.

Preferably there are used 2–3 parts by weight of solvent for part of residue.

There are utilized between 1 and 20% by weight of acid relative to saponified residue, suitably there are used 4% by weight of acid.

The mixture is heated under reflux until no more azeotrope is formed. 10 Hours is usually sufficient for completion of the reaction.

The reaction mixture is then worked up. In the preferred method the acid is washed out with aqueous sodium bicarbonate, the solvent removed by an evaporation and the residual oil distilled under reduced pressure. The distillate is then further purified, suitably by column chromotography.

The pentamethyloctalone (I) may be hydrogenated to give the corresponding pentamethyldecalone (II).

The hydrogenation is carried out in a solvent in the presence of a catalyst. Any solvent resistant to catalytic hydrogenation, which will not poison the catalyst may be used. Thus alkanols such as ethanol, and alkanoic acids such as acetic acid and the like may be utilized. Glacial acetic acid is especially preferred since good results may be obtained at room temperature, while other solvents require heating to about 40°–70°C.

Any hydrogenation catalyst may be used, among them may be mentioned palladium, platinum, platinum oxide, Raney nickel, etc. with or without a carrier. Especially preferred however is palladium on charcoal, suitably 5% palladium on charcoal at a ratio of 2–10g, preferably about 5g of catalyst/mole of octalone charged. The reaction is run at 25–100 psi suitably at about 40 psi. Any temperature may be used up to 100°C, where glacial acetic acid is used as the solvent, the reduction is carried out at ambient temperature. The hydrogenation is run until no further hydrogenation occurs.

The product was then isolated. The hydrogenation mixture is filtered, and the filtrate evaporated to yield the decalone (II) in crystalline form.

The cis-dihydrothujopsene(VI) may be oxidized to the corresponding 1,2-epoxy pentamethyldecalone (IV) which in turn is rearranged to yield the corresponding pentamethyl-1-decalone (III).

In the process the cis-dihydrothujopsene (VI) is taken up in a solvent, such as a hydrocarbon solvent preferably hexane: There added a "neutral" peracid such as peracetic, perchlorobenzoic, perbromobenzoic, perbenzoic or perchloroacetic acid.

Where the commercially available peracid contains an acidic stabilizer (i.e.1% sulfuric acid in peracetic acid) this must be removed.

The easiest method of removing the excess hydrogen ion is by addition of the salt of a weak acid suitably an acid having a pH of 3–6. Especially suitable is sodium acetate. In order to neutralize the excess acid, there are added 2 moles of the salt/mole of strong acid present, it is preferred however to use twice this amount.

There is utilized at least one mole of peracid per mole of cis-dihydrothujopsene (VI) preferably 1–1.5 mole of preferably 40% aqueous peracid.

The use of a solvent in the reaction is optional, where a solvent is used, a hydrocarbon solvent such as hexane is preferred.

The reaction is carried out at moderate temperatures suitably between 0°–50°C, although higher temperatures are permitted. It is preferred to run the reaction at between about 30°–40°C for about 15 to 30 hours, preferably for about 20 hours.

The reaction is quenched with water, the hexane and water layers separated and the aqueous layer extracted with hexane. The combined hexane extracts are washed with aqueous sodium bicarbonate and then with aqueous sodium hypo-sulfite, and water. Evaporation and distillation under reduced pressure yields the desired epoxypentamethyl decalin (IV).

The epoxide (IV) is rearranged to the corresponding ketone (III) by means of acid in a solvent.

As acids there may be used mineral acids such as sulfonic, phosphoric or perchloric, organic acids such as p-toluene sulfonic acid, Lewis acids such as boron trifluoride, or aluminum chloride. Catalysts such as magnesium bromide or magnesium iodide may also be employed. The reaction is preferably carried out in a solvent, any anhydrous solvent used in Friedel-Crafts reactions may be used. Especially preferred is the use of aluminum chloride in petroleum ether as the rearranging agent and solvent.

The quantities of acid utilized are not critical, however in order to achieve an acceptable rate of reaction these are utilized between 1 and 1.3 moles of aluminum chloride per mole of epoxide (IV). While the reaction may be run at temperatures between about 0°C and 50°C, temperatures of between about 20°C and 30°C are especially convenient. Reaction is usually complete in between about 15 and 30 minutes. The reaction is then quenched. Quenching is suitably achieved by cooling to ice bath temperatures and adding dilute aqueous sulfuric acid to the reaction mixture.

The reaction mixture is then worked up in the usual manner and the pentamethyldecane-1-one (III) is purified by distillation under reduced pressure.

EXAMPLE I

Cis-4a,5,6,7,8,8a-hexahydro-3,4a,5,5,8a-pentamethyl-2(1H)-napthalenone (I).

A mixture of 103 g (0.50 mole, 2.0 eq) of dihydrothujopsene (VI), 700 ml acetic anhydride and 250 ml glacial acetic acid was stirred at room temperature and over a period of 1½ hrs. was added at 25°, using ice bath cooling when necessary, 300 g (1.0 mole. 6.0 eg) of sodium dichromate dihydrate. After the addition, the mixture was stirred at 25° for ½ hr., using ice bath cooling when necessary, then carefully heated to 40° and maintained at 40° for 2½ hrs. with ice bath cooling when necessary.

The mixture was allowed to cool and poured into a mixture of 1 L of water and 300 ml of toluene. The layers were separated and the aq. phase extracted with toluene (2 × 300 ml). The combined toluene extract was backwashed with sat. salt solution (3 × 250 ml), dried over magnesium sulfate, and concentrated under reduced pressure.

The residual oil was distilled under nitrogen through a 15 inch glass helices packed column at 0.5 mm pressure. The first fraction (bp 72°–95°) was recovered dihydrothujopsene (VI) plus two minor oxidation by-products (15.95 g), the second fraction (bp 99°–101°) was the desired cis-4a,5,6,7,8,8a-hexahydro-3,4a,5,5,8a-pentamethyl-2 (1H)-napthalenone (I) (95% pure), 64.0 g (58% yield); $n_D^{20}$ 1.5178; mol wt. 220 (mass spectrum, $\nu$ neat .max., 1675 ($s$), 1640 ($w$), 1384 ($m$), 1367 ($m$), 1117 ($w$) cm$^{-1}$; $\lambda$MeOH max. 243 nm ($\epsilon$7, 180); nmr ($\tau$, ppm, CDCl$_3$), 3.50 (1H, quartet, J = 1.5 Hz, vinylic H), 7.49 and 7.84 (2H, AB quartet, J = 17.5 Hz, H $\alpha$ to carbonyl), 8.22 (3H, doublet, J = 1.5 Hz, vinylic methyl H), 8.58 (6H, broad absorption, methylene H), 8.91 and 8.99 12H, two singlets, methyl H). The nmr assignments were confirmed using both 60 and 100 MHz spectra.

Anal. Calcd. for $C_{15}H_{24}O$: C, 81.76; H, 10.98. Found: C, 81.53 H, 11.01.

EXAMPLE II

Cis-4a,5,6,7,8,8a-hexahydro-3,4a,5,5,8a-pentamethyl-2(1H)-napthalenone (I).

A solution of 50.0 g (0.245 mole) of thujopsene (V), 1.0 g rose bengal, and 1450 ml of distilled methanol was aerated with oxygen at 4 l./min. and irradiated with 6–15 watt green-photo GE fluorescent bulbs until the uptake of oxygen ceased as monitored by a hydroperoxide determination.

The red solution was added dropwise with slight cooling to a stirred solution of 70 g sodium sulfite in 500 ml of water. The solution was stirred overnight at room temperature, then at 70°–80° for 2 hrs., allowed to cool, diluted with 500 ml of water, and partially concentrated under reduced pressure.

The mixture was diluted with 500 ml of water and 200 ml of ether. The layers were separated, the aq. phase extracted with ether and the etherial extract was backwashed with sat. salt solution, dried, filtered, and concentrated.

A portion (10.0 g) of the crude mixture (46.6 g) was chromatographed on 350 g of alumina (neutral, act. I) packed with hexane into a 2.5 × 67 cm column. Elution with hexane and benzene gave a mixture of products (3.74 g) and these fractions were discarded. Elution with benzeneether 4:1 gave pure cis-4a,5,6,7,8,8a-hexahydro-3,4a,5,5,8a-pentamethyl-2(1H)-naphthalenone (I), 1.43 g (12–1/2% yield); the physical and spectral data was identical to that described in Example I.

EXAMPLE III

Cis-4a,5,6,7,8,8a-hexahydro-3,4a,5,5,8a-pentamethyl-2(1H)-naphthalenone (I).

Thujopsan-2-one (XV) 1.0 g was charged onto 90 g of alumina (neutral, activity 1) packed with benzene into a 1.5 × 50 cm column. Elution with benzene-ether mixtures and then with pure ether gave pure cis-4a,5,6,7,8,8a-pentamethyl-2(1H)-naphthalenone (I) (0.197 g) and elution with ether-methanol 50:1 eluted a mixture of pentamethyloctalone(I) (0.248 g, 45% overall yield) and unreacted thujopsan-2-one (XV) (0.315 g, 32%). The pentamethyloctalone I gave physical and spectral data identical to that described in Example I.

EXAMPLE IV

Cis-4a,5,6,7,8,8a-hexahydro-3,4a,5,5,8a-pentamethyl-2(1H)-naphthalenone (I).

The pentamethyloctalone (I) was prepared by the sqeuential application of the three following procedures:

A. Into a 500 ml reaction flask equipped with an agitator, thermometer, dropping funnel and condenser was charged 125 g of peracetic acid (40%, stabilized with 1% $H_2SO_4$) and while agitating heated to 35°C. Dihydrothujopsene (VI) (51.2 g) was fed in while agitating at 30°C over a 20 minute period and the batch agitated at 35°C for 3 hours. Water was added (250 ml) and the batch extracted with 3 × 50 ml of hexane.

The hexane solution was washed as follows: 2 × 50 ml of water, 1 × 50 ml of 10% $NaHCO_3$ solution, 1 × 50 ml of water, 1 × 50 ml of 10% $Na_2S_2O_5$ solution and 1 × 50 ml of water. The hexane was removed by distillation under reduced pressure leaving a residual oil (59 g) which analyzed by VPC (20M column, 225°C) as follows: (1) 1.3%, (2) 3.0% cis-dihydrothujopsene, (3) 1.4% cis-1,2,3,4,4a,8a-hexahydro-4,4,4a,6,8a-pentamethylnaphthalene (XI), (4) 0.2%, (5) 0.5% epimer of cis-3,4,4a,5,6,7,8,8a-octahydro-2,4a,8,8-8a-pentamethyl-1(2H)-naphthalenone (III), (6) 14.2% epimer of cis-3,4,4a,5,6,7,8,8a-octahydro-2,4a,8,8,8a-pentamethyl-1(2H)-naphthalenone (III), (7) 6.3% epimer of cis-1,2,4a,5,6-7,8,8a-octahydro-3,4a,5,5,8a-pentamethyl-2-naphthyl acetate (VIII), (8) 3.3% epimer of cis-1,2,4a,5,6,7,8,8a-octahydro-3,4a,5,5,8a-pentamethyl-2-naphthyl acetate (VIII), (9) 17.9% of the desired cis-4a,5,6,7,8,8a-hexahydro-3,4a,5,5,8a-pentamethyl-2(1H)-naphthalenone (I), (10) 2.4% epimer of cis-1,2,4a,5,6,7,8,8a-octahydro-3,4a,5,5,8a-pentamethyl-2-naphthol (VII), (11) 5.4% epimer of cis-1,2,4a,5,6,7,8,8a-octahydro-3,4a,5,5,8a-pentamethyl-2-naphthol (VII), (12) 2.6% cis-decahydro-1,2,-epoxy-3-acetoxy-2,4a,8,8,8a-pentamethylnaphthalene (X), (13) 33.6% cis-decahydro-1,2,-epoxy-3-hydroxy-2,4a,8,8,8a-pentamethylnaphthalene (IX), and (14) 7.5% unknown glycol.

B. The 59 g of crude material obtained as above, 10 g of potassium hydroxide, 10 ml of water and 100 ml of methanol were charged in a reaction flask and agitated under reflux (67°C) for 3 hours. Water (250 ml) was added and the methanol was distilled at atmospheric pressure until a pot temperature of 95°C was reached. The batch was extracted with 3 × 100 ml of hexane and the hexane extract was washed neutral with water. The hexane was removed by distillation leaving a residual oil (53 g) which analyzed by VPC (20M column, 225°C) as follows: (1) 2.7% XI, (2) 2.5%, (3) 1.3%, (4) 2.4%, (5) 5.2% epimer of III, (6) 9.4% epimer of III, (7) 2.7%, (8) 19.3% of the desired product I, (9) 17.9% epimer of VII, (10) 4.1% epimer of VII, (11) 1.0% epimer of IX, (12) 29.2% epimer of IV, and (13) 2.3% glycol.

C. The crude saponified mixture (53 g) obtained in the previous step was agitated under reflux with 125 ml of benzene and 2 g toluenesulfonic acid for 10 hours while removing 3.2 g of water through a water separator. The batch was washed with 2 × 50 ml of water, 1 × 25 ml of 10% $NaHCO_3$ and 1 × 50 ml of water. The benzene was distilled under slightly reduced pressure leaving a residual oil (50 g) which was vacuum distilled at 0.5 mm using a 6 inch column packed with glass helices and gave the following: (1) 6.2 g. of fractions, b.p. 80°–107°C/0.5 mm., $n_D^{20}$ 1.5012–1.5042, (2) 37 g of fractions, b.p. 107°–132°C/0.5 mm., $n_D^{20}$ 1.5060–1.5160. Fraction 1, 6.2 g, was shown by VPC to contain besides other materials (mainly hydrocarbons) 14.5% of the diene XI, 20.1% of epimers of III and 16% of the desired I. Fraction 2, 37 g, was shown by VPC to consist besides other materials (mainly hydrocarbons), 24.4% of epimers of III and 62.6% of the desired pentamethyloctalone I.

Fraction 2 (5.0 g) was chromatographed on 300 g of alumina (neutral, activity III) packed with hexane into a 2.5 × 62 cm. column. Elution, using 50 ml fractions, with hexane gave 0.33 g (7%) of hydrocarbons. Further elution with hexane and then with hexane-benzene 10:1 gave 1.65 g (33%) of a mixture of epimers of III. Continued elution with hexane-benzene 10:1 and then with hexanebenzene 1:1 gave 2.94 g (59%) of the desired pentamethyloctalone (I).

The pentamethyloctalone I gave physical and spectral data identical to that described in Example I.

EXAMPLE V

Cis-4a,5,6,7,8,8a-hexahydro-3,4a,5,5,8a-pentamethyl-2(1H)-naphthalenone (I).

Into a reaction flask equipped with an agitator, thermometer, condenser, and a water separator was charged 5 g cis-decahydro-3,4-epoxy-3,4a,5,5,8a-pentamethyl-2-naphthol (IX), prepared as described in Example VII, 0.5 g toluenesulfonic acid and 75 ml of benzene. The batch was refluxed for 23 hours while removing water through the separator. The batch was cooled to room temperature and washed with 2 × 50 ml of water, neutralized with 10% sodium bicarbonate and washed with 2 × 50 ml of water. The benzene was removed by distillation under reduced pressure leaving a residual 4.5 g of crude product, which was vacuum distilled at 0.4 mm using a micro distillation head. The following fractions were collected: (1) 0.2 g (b.p. 102°C/0.4 mm., $n_D^{20}$ 1.5115); (2) 2.7 g (b.p. 105°–123°C/0.4 mm., $n_D^{20}$ 1.5130), (3) 0.9 g of residue. Fraction 2 analyzed by VPC (225°C, 20M) as containing 7 components: (1) 0.3%, (2) 1.8%, (3) 6.7%, (4) 5.6%, (5) 76.2%, (6) 2.8%, (7) 6.5%. A sample of compoennt 5 was isolated by VPC (225°C 20M) and shown by spectral data to be cis-4a,5,6,7,-8,8a-hexahydro-3,4a,5,5,8a-pentamethyl-2(1H)-naphthalenone (I), identical to (I) prepared in Example I.

EXAMPLE VI

Cis-4a,5,6,7,8,8a-hexahydro-3,4a,5,5,8a-pentamethyl-2(1H)-naphthalenone (I).

Into a 50 ml reaction flask equipped with an agitator, thermometer, dropping funnel and a condenser was charged 2.5 g peracetic acid (40% containing 1% $H_2SO_4$ stabilizer). The batch was agitated and heated to 35°C and 2.2 g of epoxydihydrothujopsene (IV), as prepared in Example IX, was added over a 25 minute period at 35°C and the batch agitated at 35°C for 3½hours. The batch was diluted with water and extracted with 2 × 50 ml of benzene. The benzene extract was washed with water, washed with 10% sodium bicarbonate, and then washed with water until neutral. The benzene was removed by distillation under reduced pressure leaving a residual crude of 2 g which analyzed by VPC (20M column, 225°C) as follows: (1) 0.4%, (2) 0.4% dihydrothujopsene (VI), (3) 4.9% cis-1,2,3,4,4a8a-hexahydro-4,4,4a,6,8a-pentamethyl-naphthalene (XI), (4) 3.0%, (5) 1.6% epimer of cis-3,4,4a-5,6,7,8,8a-octahydro-2,4a,8,8,8a-pentamethyl-1(2H)-naphthalenone (III), (6) 16.9% epimer of cis-3,4,4a,5,6,7-8,8a-octahydro-2,4a,8,8,8a-octahydro-2,4a,8,8,8a-pentamethyl-1(2H)-naphthalenone (III), (7) 10.0% epimer of cis-1,2,4a,5,6,7,8,8a-octahydro-3,4a,5,5,8a-pentamethyl-2-naphthyl acetate (VIII), (8) 12.5% epimer of cis-1,2-4a,5,6,7,8,8a-octahydro-3,4a,5,5,8a-pentamethyl-2-naphthyl acetate (VIII), (9) 17.3% of the desired cis-4a,5,6,7,8,8a-hexahydro-3,4a,5,5,8a-pentametnyl-2(1H)-naphthalenone (I), (10) 2.2% epimer of cis-1,2,4a,5,6,7,8-8a-octahydro-3,4a,5,5,8a-pentamethyl-2-naphthol (VII), (11) 2.1% epimer of cis-1,2,4a,5,6,7,8,8a-octahydro-3,4a-5,5,8a-pentamethyl-2-naphthol (VII), (12) 4.0% cis-decahydro-1,2-epoxy-3-acetoxy-2,4a,8,8,8a-pentamethyl-naphthalene (X), (13) 21.0% cis-decahydro-1,2-epoxy-3-hyroxy-2,4a,8,8,8a-pentamethylnaphthalene (IX), and (14) 4.6% unknown glycol.

This above result is identical to the results in Example IV, which uses dihydrothujopsene (VI) as the starting material. The material can be converted by saponification followed by dehydration to the desired pentamethyloctalone (I), pentamethyl-1-decalone(III) and diene(XI) as described in procedure B and C of Example IV.

EXAMPLE VII

| | |
|---|---|
| cis-1,2,4a,5,6,7,8,8a-Octahydro-3,4a,5,5,8a-pentamethyl-2-naphthol | (VII) |
| cis-Decahydro-3,4-epoxy-3,4a,5,5,8a-pentamethyl-2-naphthol | (IX) |
| cis-1,2,3,4,4a,8a-Hexahydro-4,4,4a,6,8a-pentamethylnaphthalene | (XI) |

Example IV was repeated for the purpose of the isolation and characterization of the compounds, cis-1,2,4a,5,6,7,8,8a-octahydro-3,4a,5,5,8a-pentamethyl-2-naphthol (VII), cis-decahydro-3,4-epoxy-3,4a,5,5-,8a-pentamethyl-2-naphthol (IX), and the diene, cis-1,2,3,4,4a,8a-hexahydro-4,4,4a,6,8a-pentamethyl-naphthalene (XI) which are formed in this example.

One hundred fifty grams (150 g) of dihydrothujopsene (VI) was processed as described in Example IV, section A and gave crude material, (168 g) which was dissolved in hexane (450 ml). The hexane solution cooled to 10°C gave solid crystals which after filtering and air drying gave 17 g of crystalline IX, m.p. 140–142.5°C.

A small sample of IX was recrystallized from methanol and vacuum dried. The product analyzed as follows: m.p. 143.5°–144.5°C; saponification value after acetylation 199.1; $\nu$KBr max., 3490 (s), 1375 (w), 1368 (s), 1355 (w), 1332 (m), 1318 (m), 1304 (m), 1290 (m), 1262 (w), 1242 (m), 1230 (m), 1198 (w), 1088 (s), 1065 (s), 1048 (s), 1027 (s), 1004 (s), 972 (w), 912 (m), 872 (s), 820 (m), 785 (m), 702 (m), 640 (w); NMR ($\tau$,ppm,CDCl$_3$), 6.15 (1H, triplet, J = 7, $\alpha$H to OH), 6.97 (1H, singlet, epoxide H), 8.00 (2H, broad, $\beta$H to C— OH). 8.62 (3H, singlet, epoxide methyl), 8.95 (3H, singlet, CH$_3$), 8.98 (3H singlet, CH$_3$), 9.06 (6H, singlet, 2CH$_3$), 8.5–9.0 (6H, multiplet, 3CH$_2$); Mass spectra, 220 ion which is M-18 (H$_2$O).

Anal. Calcd. for $c_{15}H_{26}O_2$: C, 75.58; H, 11.00. Found: C, 75.55; H, 11.03. 18

The hexane was removed by distillation at atmospheric pressure and the residue (151 g) was vacuum distilled at 0.6 mm using a distillation head and gave the following:

1. 15 g of fractions (b.p. 85°–140°C/0.6 mm., mainly hydrocarbons),
2. 114.5 fractions (b.p. 140°–155°C/0.6 mm), and
3. 11.0 g residue. The 114.5 g fractions on standing partially crystallized. The crystals were filtered and washed with cold hexane. The dried crystals amounted to 19 g, m.p. 140°–142.5°C and were identical to compound IX above.

The mother liquor from the crystals was distilled under vacuum to remove the hexane and the residual material (saponification value 85.9) was saponified by refluxing for 6 hours with 15 g potassium hydroxide, 15 ml of wateer and 100 ml of methanol. The reaction was worked up as described in Example IV section B and gave 77 g of crude material which was vacuum distilled at 0.6 mm using a 6 inch column packed with glass helices and the following fractions collected:

1. 29.0 g (b.p. 96°–105°C/0.6 mm),
2. 31.8 g (b.p. 105°–115°C/0.6 mm)
3. 10.2 g (b.p. 115°–127°C/0.6 mm. Fractions 2 and 3 partially crystallized on standing. Recrystallization from hexane of the crystals (6.9 g) from fraction 2 gave pure VII which analyzed as follows: m.p. 122°–123°C; mol wt. 222 (mass spectrum; KBr max., 3220 (s), 1395 m) 1380 (s), 1365 (m), 1333 (m), 1280 (s), 1195 (w), 1122 (w), 1090

(m), 1075 (m), 1055 (s), 1040 (m), 1012 (s), 978 (w), 960 (w), 932 (m), 900 *w), 853 (m), 802 (w); NMR (τ, ppm,CDCl$_3$), 4.55 (1H, singlet, vinylic H), 5.98 (1H triplet, J=6.5 Hz, Hα to C—OH), 8.27 (3H, singlet, vinylic CH$_3$), 8.97 (3H, singlet CH$_3$), 9.00 (3H singlet, CH$_3$), 9.05 (6H, singlet 2CH$_3$), 8.38–8.90 (8H, multiplet, 4CH$_2$).

Fractions 1, 3, and the mother liquid from fraction 2 above were combined and 51 g of this material was refluxed with 125 ml of benzene and 2.0 g p-toluenesulfonic acid for 12 hours while removing water through a water separator. The batch was worked up as described in Example IV, section C., and gave 50 g of crude material which was vacuum distilled at 0.5 mm using a 6 inch column packed with glass helices and the following fractions collected: (1) 2.0 g (b.p. 80°C/0.5 mm.), (2) 13.5 g (b.p. 80°–105°C), (3) 26.5 g (b.p. 105–116/0.5 mm.) and 7.0 g of residue. Fraction 1 was pure cis-1,2,3,4,4a-8a-hexahydro-4,4,4a,6,8a-pentamethylnaphthalene (XI) and fraction 2 was principally cis-1,2,3,4,4a,8a-hexahydro-4,4,4a,6,8a-pentamethylnapthalene (XI).

Fraction 1 (XI) analyzed as follows: mol. wt. 204 (mass spectrum; νneat max., 1654 (m), 1382 (s), 1373 (s), 1363 (m), 1340 (w), 1180 (w), 1117 (w), 1078 (w), 1025 (m), 970 (m), 845 (m), 826 (m), 745 (m), 735 (s); NMR (τ,ppm,CDCl$_3$) centered at 4.47 (2H, multiplet, 2vinylic H), centered at 4.94 (1H, w$^h$/2 = 5Hz, vinyl H), 8.28 (3H, doublet J=1.5 Hz, vinylic CH$_3$), 8.97 (3H, singlet, CH$_3$), 9.00 (3H, singlet, CH$_3$), 9.12 (3H, singlet, CH$_3$), 9.18 (3H, singlet, CH$_3$), 8.45–8.85 (6H, multiplet, 3CH$_2$).

Fraction 3 (26.5 g) was shown by VPC to consist principally (93.1%) of three components: (A) 18.8%, (B) 21.5% and (C) 52.8%. Samples of each of the components were isolated by VPC (225°C, 20M) and shown by IR and NMR that A and B were epimers of pentamethyl-1-decalone III, Example X, and C was pentamethyloctalone I, Example I.

EXAMPLE VIII

Cis-3,4,4a,5,6,7,8,8a-octahydro-3,4,a,5,5,8a-pentamethyl-2-(1H)-naphthalenone (II).

A mixture of 17.7 g (0.0805 mole) of pentamethyloctalone I, 100 ml of glacial acetic acid, and 0.5 g of 5% palladiim on carbon was hidrogenated at room temperature on a Parr shaker under an atmosphere of 40 psi of hydrogen until the hydrogen uptake ceased. The solvent was removed under reduced pressure and the crude crystalline material (18.7 g) was recrystallized twice from methanol to give cis-3,4,4a,5,6,7,8,8a-octahydro-3,4a,5,5,8a-pentamethyl-2-(1H)-napthalenone (II) as white needles, 8.45 g (50% yield): mp 111.0°–113.5°; mol. wt. 222 (mass spectrum) νKBr max. 1700 (s), 1440 (s), 1368 (m), 1356 (w), 1232 (w), 1184 (w), 1124 (w), 1096 (w), cm$^{-1}$; NMR (τ, ppm, CDCl$_3$, 60 MHz), 7.12–8.00 (3H, multiplet, H alpha to the carbonyl), 8.01– 8.74 (8H, multiplet, methylene H), 8.79, 8.88, 8.90, and 9.14 (four singlets, four tertiary methyl groups), 9.02 (doublet, J= 6 Hz, secondary methyl group). The total methyl region integrated for 15H.

Anal. Calcd. for C$_{15}$H$_{26}$O; C,81.02; H, 11.79. Found: C, 80.99; H, 11.93.

EXAMPLE IX

Cis-decahydro-1,2-epoxy-2,4a,8,8,8a-pentamethylnaphthalene (IV).

Into a reaction flask equipped with agitator, thermometer, and dropping funnel was charged 150 g of dihydrothujopsene (VI), 300 ml hexane and 50 g anhydrous sodium acetate. The batch was agitated and heated to 40°C and 172 g peracetic acid (40%) was fed in over a ½ hour period at 40°C. The batch was agitated at 40°C for 17 hours. Peracetic acid (30 g) was added and agitation continued 3 hours at 40°C.

300 ml of water was added and the hexane and aqueous layers separated. The aqueous layer was extracted with 3 × 100 ml of hexane. The combined extract was washed with 1 × 100 ml of water, neutralized with 10% NaHCO$_3$, washed with 1 × 100 ml of 10% Na$_2$S$_2$O$_5$ and washed with 1 × 50 ml of water. The hexane was removed under reduced pressure and the crude material (160 g) distilled on a 37 cm column packed with glass helices to give the following fractions: (1) 15.2 g (b.p. 74°–76°C/0.5 mm., 51% dihydrothujopsene (VI), 49% cis-decahydro-1,2-epoxy-2,4a,8,8,8a-pentamethylnaphthalene (IV), (2) 32.0 g (b.p. 76°C/0.5 mm., 20% dihydrothujopsene (VI), 80% cis-decahydro-1,2-epoxy-2,4a,8,8,8a-pentamethylnaphthalene (IV), (3) 92.9 g (b.p. 76-81°C/0.5 mm.) of the desired cis-decahydro-1,2-epoxy-2,4a8,8,8a-pentamethylnaphthalene (IV), 4) 8.3 g (b.p. 81–83°C/0.5 mm., 80% cis-decahydro-1,2-epoxy-2,4a,8,8,8a-pentamethylnaphthalene (IV)), (5) 5.0 g of residue.

The cis-decahydro-1,2-epoxy-2,4a,8,8,8a-pentamethylnaphthalene (IV) (90.5% yield) analyzed as follows: $n_D^{20}$ 1.4965; sp.gr.25°C/25°C: 0.0978; VPC (20M column, 225°C) two components, 1) 5.5%, 2) 94.5%; mol. wt. 222 (mass spectrum).

Anal. Calcd. for C$_{15}$H$_{26}$O: C, 81.02, H, 11.79. Found: C, 81.21, H, 11.74.

The two components of the epoxypentamethyldecalin IV were separated in a pure form by VPG (210°C, 20M column). The minor isomer analyzed as follows: mol. wt. 222 (mass spectrum); ν neat max. 1395 (s), 1378 (s), 1370 (s), 1245 (m), 1210 (m), 1110 (m), 1046 (m), 1037 (m), 1020 (m), 962 (w), 940 (w), 918 (m), 886 (s), 815 (s), 762 (w), 705 (w), 582 (m); NMR (τ,ppm,CDCL$_3$), 7.33 (1H, singlet α-H), 8.74 (3H, singlet, CH$_3$), 8.96 (6H, singlet, 2CH$_3$), 9.02 (3H, singlet, CH$_3$), 9.09 (3H; singlet, CH$_3$), 7.65–8.70 (SH, complex multiplet, 4CH$_2$).

The major isomer analyzed as follows: mol. wt. 222 (mass spectrum); ν neat max., 1397 (s), 1380 (s), 1334 (w), 1200 (w), 1180 (w), 1120(w), 1090 (w) 1076 (w), 1038 (w), 1005 (w), 980 (w), 945 (w), 930 (w), 920 (w), 905 (w), 870 (m), 862 (m), 820 (m); NMR (τ,ppm,CDCl$_3$),7.16 (1H, singlet, α-H), 8.71 (3H, singlet, α-CH$_3$), 8.94 (6H, singlet, 2CH$_3$), 9.03 (6H, singlet, 2CH$_3$).

The above data shows the two compounds are epimers.

EXAMPLE X

Cis-3,4,4a,5,6,7,8,8a-octahydro-2,4a,8,8,8a-pentamethyl-1 (2H)-naphthalenone (III).

Into a reaction flask equipped with an agitator, thermometer, condenser, drying tube and a nitrogen inlet tube was charged 17.7 g of aluminum chloride and 100 ml of petroleum ether. The batch was placed under an atmosphere of nitrogen and a mixture of 25 g of the epoxypentamethyldecalin (IV), prepared as in Example IX, in 25 ml of petroleum ether was added while agitating over a 17 minute period at 25° to 30°C with slight cooling. The batch was agitated at 25°C for 1 hour and cooled to − 5°C. A solution of 300 ml of 5% sulfuric acid was added and agitated at − 5°C for ½ hour and then an additional 1½ hours allowing the temperature to rise to room temperature. The petroleum ether layer was separated and the aqueous layer extracted with 2 × 50 ml of petroleum ether. The combined ether layers were washed with water, neutralized with 10% $NaHCO_3$ solution and washed neutral with water. The petroleum ether was removed under reduced pressure leaving a residual (25 g) which was vacuum distilled at 0.5 mm. using a 6 inch column packed with glass helices and the following fractions collected:

(1) 6 g (b.p. 85°–88°C, $n_D^{20}$ 1.5015–1.5025), (2) 14.5 g (b.p. 88°–120° C, $n_D^{20}$ 1.5026 –1.5040), and 2 g of residue.

Redistillation of fractions 1 and 2 gave 4 g hydrocarbons (b.p. 85°–87°C. $n_D^{20}$ 1.5018), and 16 g (b.p. 98°–105°C, $n_D^{20}$ 1.5026) of the desired product, cis-3,4,4a-5,6,7,8,8a-octahydro-2,4a,8,8,8a-pentamethyl-1(2H)-naphthalenone (III). Yield: 64%).

Analysis: Mass Spectrum, mol.wt. 222: Calcd for $C_{15}H_{26}O$: C, 81.02%; H, 11.79%; Found: C, 81.08%; H, 11.67%; VPC (225°C, 20m column) two components 15% (minor), 85% (major).

A small sample of the major isomer was prepared pure by VPC (225°C, 20M column) and was solid. A small sample of the mixture of epimers was seeded with the crystals, cooled over night at 0°C and the material partially crystallized. The crystals were filtered, recrystallized twice from methanol and vacuum dried, m.p. 43.5°– 44.5°C. The VPC showed this to be the major epimer of III which analyzed as follows: mol. wt. 222 (mass spectrum): $\nu$ neat max. 1690 (s), 1388 (s), 1375 (m), 1318 (w), 1240 (w ), 1145 (m), 1092 (m), 1040 (w), 980 (m), 952 (w), 822 (w), 774 (w), $CM^{-1}$; NMR ($\tau$, ppm,$CDCl_3$), centered at 750 (2H, consisting of an octet), centered at 8.20 (1H, consisting of a broad multiplet), 8.81 (3H, singlet, $CH_3$), 8.97 (3H, doublet, J = 6.5 Hz, $CH_3$), 8.96 (3H, singlet, $CH_3$), 9.16 (3H, singlet, $CH_3$), 9.19 (3H, singlet, $CH_3$), 8.30–8.75 (8H, complex multiplet, $4CH_2$).

A small sample of the minor isomer was prepared pure by VPC (225°C, 20M column) and was solid. The sample analyzed as follows: mol. wt. 222 (mass spectral); $\nu$ neat max. 1705 (s), 1395 (m), 1378 (m), 1320 (w), 1197 (w), 1158 (w), 1112 (w), 1036 (w), 978 (m), 938 (w), 842 (w), 810 (w), $cm^{-1}$; NMR ($\tau$, ppm, $CDCl_3$), centered at 7.17 (1H, septet. J=6.5 Hz, αH to C=O), 8.76 (3H, singlet, $CH_3$), 8.92 (3H, singlet, $CH_3$), 8.99 (6H, singlet, $2CH_3$), 9.11 (3H, doublet, J = 6.5 Hz, $CH_3$), 7.60 –8.85 (10H, complex multiplet. 5 $CH_2$).

EXAMPLE XI — Base Cologne Formulation

There was prepared a citrus cologne base which was used to test the aromatic properties of compounds (I–IV). These results are set forth in Examples XII-–XV infra: The base had the following composition

| | |
|---|---|
| Benzyl isoeugenol | 26 |
| Bergamot oil | 286 |
| Geranium oil | 10 |
| Lavender oil | 31 |
| Lemon oil | 265 |

-continued

| | |
|---|---|
| Lime oil | 53 |
| Neroli oil | 10 |
| Orange bitter oil | 138 |
| Orange sweet oil | 74 |
| Rosemary oil | 31 |
| Sage, clary oil | 21 |
| Thyme oil (white) | 5 |
| | 950 |

EXAMPLE XII

Use of cis-4a,5,6,7,8,8a-hexahydro-3,4a,5,5,8a-pentamethyl-2(1H)-naphthalenone (I) in a cologne base of Ex. XI Cis-4a,5,6,7,8,8a-hexahydro-3,4a,5,5,8a-pentamethyl-2(1H)-naphthalenone (I) has a strong green woody peppery odor and lasts approximately two weeks on a blotter. The addition of 5% of (I) to the above cologne base adds great strength and lift to the fragrance while contributing a diffusive woody character on dry out. The cologne base without (I) is not as bright nor as pleasing as that with the derivative. This material also has fixative properties which produces a better balanced and more pleasing bouquet of the cologne as compared to the cologne base without it. The cologne base containing this material produces a fragrance that lasts approximately twice as long as the cologne without this material. The material has a very intense odor and may generally be used from 0.1% to 25% by weight. Higher concentrations (25% to 90%) may also be used successfully for unique and special effects.

EXAMPLE XIII

Use of cis-3,4,4a,5,6,7,8,8a-octahydro-3,4a,5,5,8a-pentamethyl-2(1H)-naphthalenone (II) in a Cologne Base of Ex. XI Cis-3,4,4a,5,6,7,8,8a-octahydro-3,4a,5,5,8a-pentamethyl-2(1H)-naphthalenone (II) has a strong woody amber odor which lasts approximately two weeks on a blotter. The addition of 5% of this material to the above cologne base contributes an extremely fresh amber character to the fragrance. The cologne without (II) is not as fresh nor does it have the lift and body of that with (II). This material also has fixative properties which produce a better balanced and more pleasing bouquet of the cologne as compared to the cologne base without it. The cologne base containing this material producees a fragrance that lasts approximately twice as long as the cologne without this material. The material may generally be used in concentration ranging from 0.1% to 25% by weight. Higher concentrations (25% to 90%) may also be used successfully for unique and special effects.

EXAMPLE XIV

Use of cis-3,4,4a,5,6,7,8,8a-octahydro-2,4a,8,8,8a-pentamethyl-1(2H)-naphthalenone (III) in a Cologne Base of Ex. XI Cis-3,4,4a,5,6,7,8,8a-octahydro-2,4a,8,8,8a-pentamethyl-1(2H)-naphthalenone (III) has a warm woody odor which lasts approximately 2 weeks on a blotter. The addition of 5% of this material to the above cologne base contributes lift and strength together with a pleasing woody character on dry-out. The cologne without (III) is thin and lacks the unique odor qualities contributed by this aroma chemical. This material also has fixative properties which produces a better balanced and more pleasing bouquet of the cologne as compared to the cologne base without it. The cologne base containing this material produces a fragrance that lasts approximately twice as long as the cologne without this material. This material may be generally used in concentrations ranging from 1% to 25% by weight. Higher concentrations (25% to 90%) may be used successfully for unique and special effects.

EXAMPLE XV

Use of cis-decahydro-1,3-epoxy-2,4a,8,8,8a-pentamethylnaphthalene (IV) in a Cologne Base of Ex. XI Cis-decahydro-1,2-epoxy-2,4a,8,8,8a-pentamethylnaphthalene (IV) has a pleasant woody cedar odor which lasts approximately two weeks on a blotter. The addition of 5% of this material to the above cologne base contributes a fresh diffusive woodyness to the fragrance as a whole and adds warmth to the dryout. The cologne without (IV) lacks body and is not as desirable a fragrance as that with (IV). This material also has fixative properties which produce a better balanced and more pleasing bouquet of the cologne as compared to the cologne base without it. The cologne base containing this material produces a fragrance that lasts approximately twice as long as the cologne without this material.

This material may generally be used in concentrations ranging from 1 to 25%. Higher concentrations (25 to 90%) may also be used successfully for unique and special effects.

EXAMPLE XVI

Use of the Pentamethyloctalone I as a Sandelwood Component.

The pentamethyloctalone I when compounded with Sandela makes a major odor contribution to the building of a synthetic sandelwood. This is demonstrated in the following base:

| | |
|---|---|
| Pentamethyloctalone I | 200 |
| Sandela (Givaudan Corp.) | 700 |
| Amyris oil | 50 |
| Am. Cedarwood oil | 50 |
| | 1000 |

The addition of I produces a fatty-woody character which is observed in sandelwood. It contributes a more natural sandelwood note to the above formulation and is considered important to the formulation of a synthetic sandelwood base. In such a formulation, I may be used over a range of 5% to 60% by weight.

EXAMPLE XVII

Use of the Pentamethyl-2-decalone II, the Pentamethyl-1-decalone III and the Epoxypentamethyldecalin IV as Sandelwood Components.

The pentamethyl-2-decalone II, the pentamethyl-1-decalone III and the epoxypentamethyldecalin IV are not as outstanding by themselves as pentamethyloctalone I in the above synthetic sandelwood formulation. However, they do contribute unique notes to this type of formulation when used together with I. The following formulae demonstrates:

| | A | B | C |
|---|---|---|---|
| Pentamethyloctalone I | 200 | 200 | 200 |
| Sandela | 600 | 600 | 600 |
| Amyris oil | 50 | 50 | 50 |
| Cedarwood oil (Am.) | 50 | 50 | 50 |
| Epoxypentamethyldecalin IV | 100 | — | — |
| Pentamethyl-1-decalone III | — | 100 | — |
| Pentamethyl-2-decalone III | — | — | 100 |
| | 1000 | 1000 | 1000 |

Both III and IV contribute lift and warmth to the formulation and improve the odor, making A and B closer still to natural sandelwood. The pentamethyl-2-decalone II adds a unique fresh amber woody character to the topnote while contributing a soft woodyness to the body of the fragrance which enhances the natural sandelwood character.

What is claimed is:
1. A compound of the formula

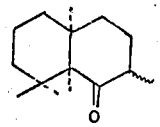

* * * * *